US00PP34976P3

(12) United States Plant Patent
Wright et al.

(10) Patent No.: US PP34,976 P3
(45) Date of Patent: Feb. 14, 2023

(54) BLUEBERRY PLANT NAMED 'C12-069'

(50) Latin Name: ***Vaccinium corymbosum* hybrid**
Varietal Denomination: 'C12-069'

(71) Applicants: CostaExchange Pty Ltd, Ravenhall (AU); FLORIDA FOUNDATION SEED PRODUCERS, INC., Marianna, FL (US)

(72) Inventors: Gary Wright, Arrawarra Headland (AU); Paul M. Lyrene, Micanopy, FL (US)

(73) Assignees: CostaExchange Pty Ltd, Revenhall (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/803,053

(22) Filed: Jan. 26, 2022

(65) Prior Publication Data

US 2022/0248587 P1 Aug. 4, 2022

Related U.S. Application Data

(60) Provisional application No. 63/206,154, filed on Jan. 29, 2021.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

*Primary Examiner* — Susan McCormick Ewoldt
(74) *Attorney, Agent, or Firm* — Baker & McKenzie LLP

(57) ABSTRACT

The new blueberry plant variety 'C12-069' is provided. 'C12-069' is a commercial variety intended for the fresh market. The variety is produced from a cross of 'Indigocrisp' (seed parent, U.S. Plant Pat. No. 26,523) and 'FL01-271' (unpatented pollen parent).

5 Drawing Sheets

Latin name of the genus, and species:
Genus—*Vaccinium.*
Species—*corymbosum* hybrid.
Variety denomination: The new blueberry plant claimed is of the variety denominated 'C12-069'.

BACKGROUND OF THE INVENTION

The new variety 'C12-069' was selected from a population of seedlings derived from crossing the blueberry varieties known as 'FL98-325' (seed parent) (U.S. Plant Pat. No. 26,523) and the variety known as 'FL01-271' (unpatented pollen parent). The cross was made in 2006 in Florida, USA and the seed was sown and grown in Corindi Beach, New South Wales, Australia. The new variety was selected in 2012 from among plants located on land at Corindi Beach and assigned the breeding code 'C12-069'. Plants of 'C12-069' were propagated by cuttings for further evaluation and resulted to be uniform and stable. The new variety showed distinctive traits such as evergreen, with fruit of good flavor, large fruit size, and firmness.

SUMMARY OF THE INVENTION

The new variety 'C12-069' was originated from a cross of 'FL98-325' (seed parent) (U.S. Plant Pat. No. 26,523) and the variety known as 'FL01-271' (unpatented pollen parent) in 2006 in Florida, USA.

The new blueberry variety resulted from seedlings produced in a controlled breeding programme. The cross was made in 2006 in Florida, USA and the seed was sown and grown in Corindi Beach, New South Wales, Australia.

The new variety was selected in 2012 from among plants located on land at Corindi Beach and has since been named 'C12-069'. Since then plants of 'C12-069' were propagated by cuttings for further evaluation and confirmed to be uniform and stable. Asexual reproduction of the new variety 'C12-069' by cutting propagation since 2012 at Corindi Beach, New South Wales, Australia has demonstrated that the new variety reproduces true to type plants.

The new variety was selected in 2012 as a single plant within a population of seedlings resulting from controlled cross of *Vaccinium* varieties. The seedling population was planted in an experimental block in the field at Corindi Beach, New South Wales, Australia and the selection of the new variety took place in the same block. Selection criteria were a combination of early cropping time, between the very early to early cropping variety 'Snowchaser' (U.S. Plant Pat. No. 19,503P3) and the early to mid season cropping variety 'C99-42' (U.S. Plant Pat. No. 20,695P2). 'C12-069' has estimated low chilling requirement between 150 to 300 hours, is non-deciduous type of plant (evergreen), very large fruit size, good fruit flavor, firm fruit and long shelf life. The new variety was subsequently evaluated for seven years at the commercial farm at Corindi Beach, New South Wales, Australia.

The following characteristics of the new variety have been repeatedly observed and can be used to distinguish 'C12-069' as a new and distinct variety of *Vaccinium corymbosum* hybrid:

1. Non-deciduous (Evergreen)
2. Early season crop
3. Very large fruit size (4.1 g average)

4. Low chilling requirement
5. Excellent firmness and good flavor
6. Long shelf life The new blueberry variety 'C12-069' has maintained its distinguished characteristics throughout successive asexual propagation. The variety has been repeatedly asexually reproduced through softwood cuttings in New South Wales, Australia and the clones are phenotypically identical to the original plant.

BRIEF DESCRIPTION OF THE DRAWINGS

The accompanying photographic illustration shows typical specimens in full color of the foliage and fruit of the new variety 'C12-069'. The colors are as nearly true as is reasonably possible in a color representation of this type.

Figure 1:
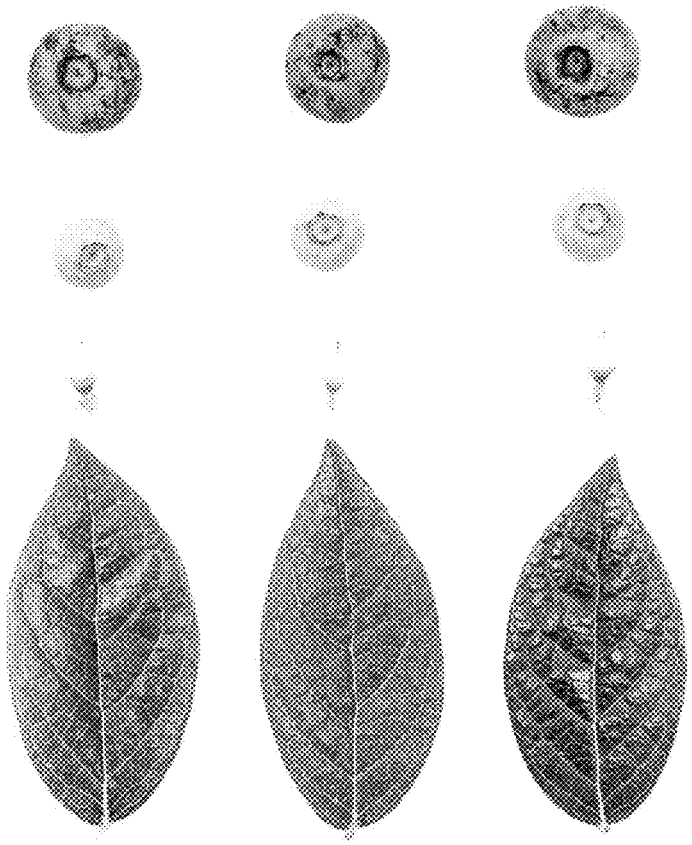
FIG. 1 is a photograph of the new variety 'C12-069' showing botanical parts of the plant (ripe fruit, green fruit, flowers and leaves).
Figure 2:
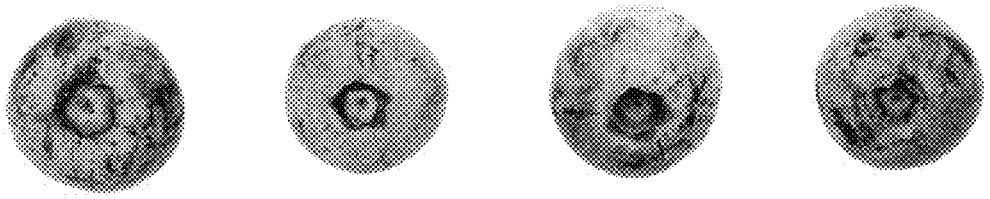
FIG. 2 is a photograph of the new variety 'C12-069', showing a typical fruit calyx of the variety.
Figure 3:
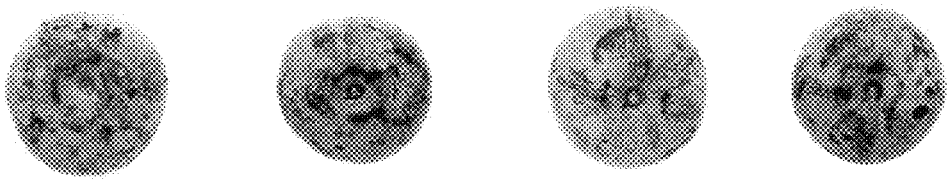
FIG. 3 is a photograph of 'C12-069' showing a typical pedicel scar of a fruit of the variety.
Figure 4:
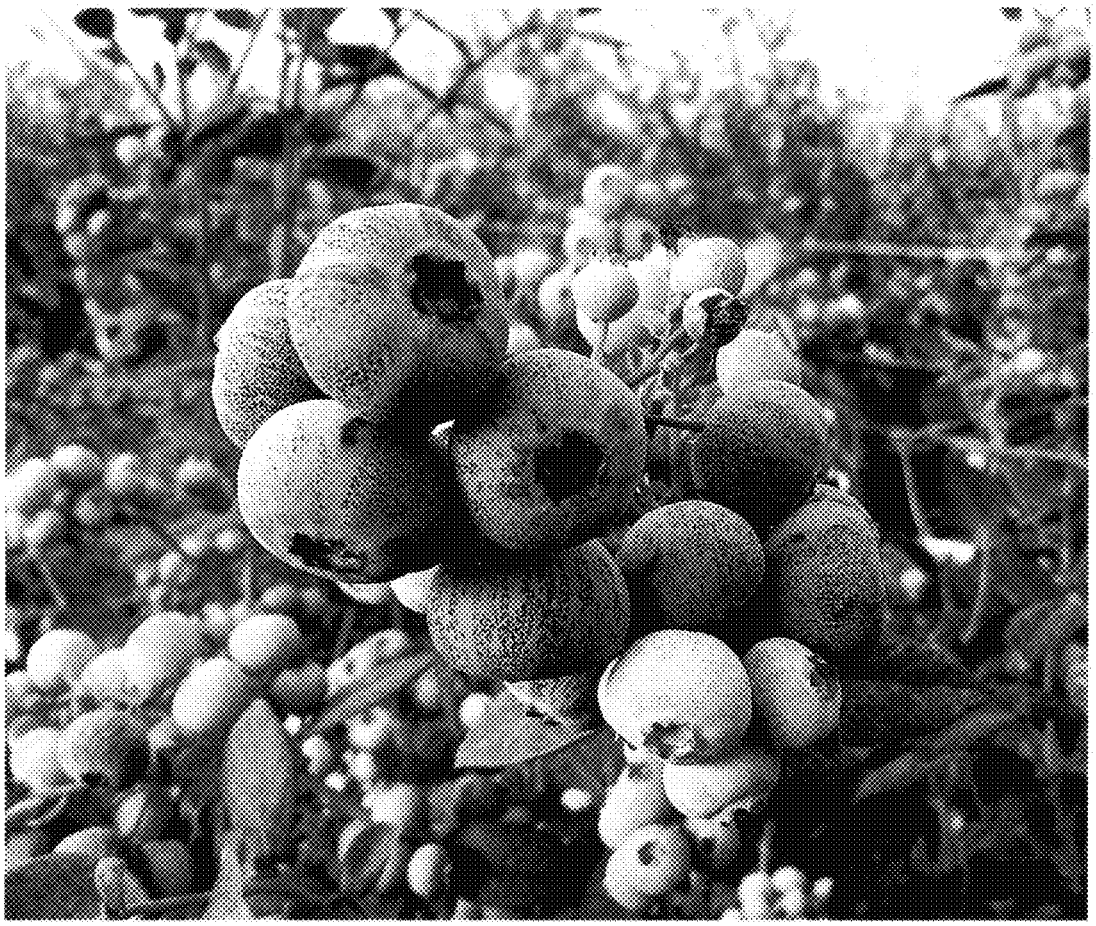
FIG. 4 shows the typical fruit cluster of the new variety 'C12-069'.
Figure 5:
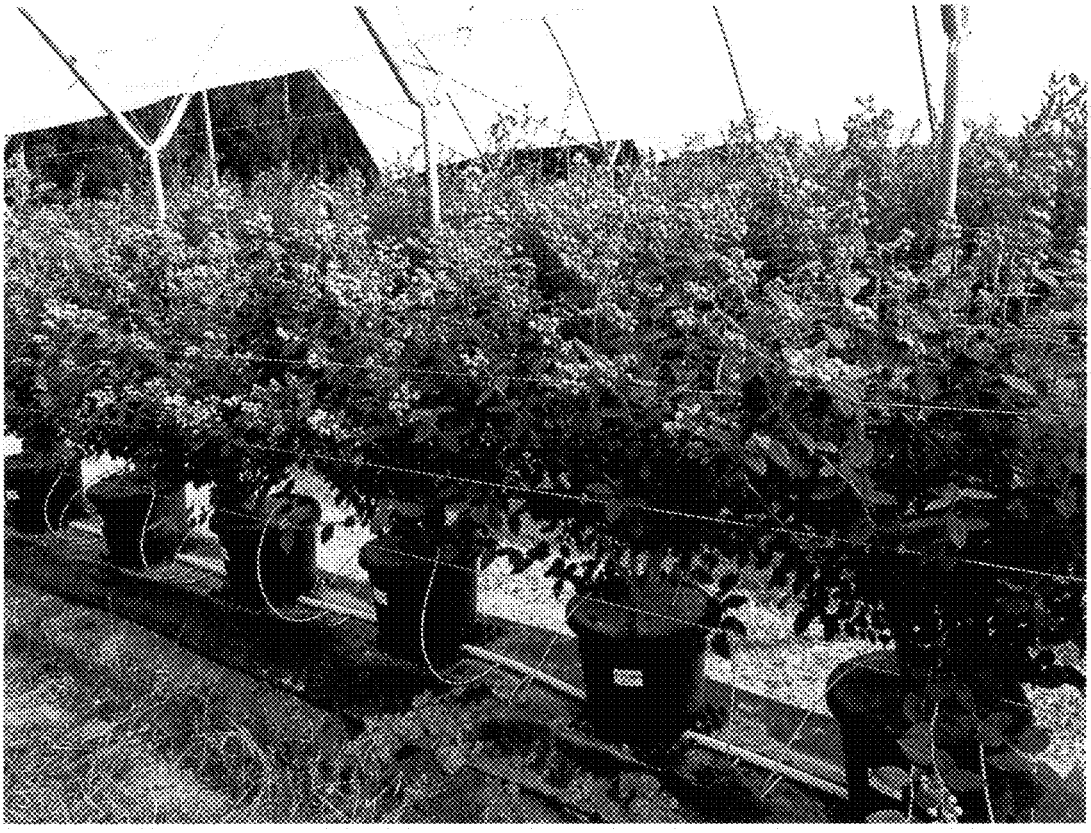
FIG. 5 shows a full row of the new variety 'C12-069' growing in pots and managed in substrate.

The colors in the photographs are as close as possible with the photographic and printing technology utilized. The color values cited in the detailed botanical description accurately describe the colors of the new blueberry variety.

DETAILED BOTANICAL DESCRIPTION

The following detailed description sets forth the distinctive characteristics of 'C12-069'. The data which defines these characteristics was collected from asexual reproductions of the original selection. Dimensions, sizes, colors, and other characteristics are approximations and averages set forth as accurately as possible. For all traits data was collected from 3 plant parts across 6 randomly selected plants. For the traits relating to fruits (e.g., fruit weight, firmness, brix, acidity) the data is an average across twenty fruits collected randomly. The plant history was taken on plants approximately 3 years of age, and the descriptions relate to plants grown in the field in Corindi Beach, New South Wales, 2456 Australia. Descriptions of fruit characteristics were made on fruit grown in Corindi Beach, New South Wales, 2456 Australia. Color designations are from the 2007 edition of The Royal Horticultural Society ("R.H.S.") Colour Chart. 'C12-069' has not been observed under all possible environments. The phenotype may vary slightly with different growing environments such as temperature, light, fertility, soil pH, moisture, and maturity levels, but without any change in the genotype.

Classification:

a. *Family*.—Ericaceae.
b. *Genus*.—*Vaccinium*.
c. *Species*.—*Corymbosum* hybrid.
d. *Common name*.—Blueberry.

Parentage:

*Female parent*.—Patented variety 'FL98-325'.
*Male parent*.—Unpatented selection 'FL01-271'.

Market class: Fresh market.

PLANT

General:

*Parentage*.—'FL98-325' x 'FL01-271'.
*Plant height*.—1.44 m.
*Plant width*.—0.92 m.
*Growth habit*.—Upright.
*Growth*.—Vigour is medium to low.
*Mature cane length*.—0.60 m.
*Mature cane width*.—16.8 mm.
*Mature cane color*.—Grey-orange group 165B.
*Bark texture*.—Smooth to medium.
*Fruiting wood in length*.—58.0 cm.
*Productivity*.—Medium to low yield. Average of 3 Kg per plant (estimated equivalent production of 6.7 pounds per plant) from 3-year-old plants when growing in 17 L pots at Corindi Beach, NSW. The plants are spaced at 0.7 m apart along the row and 2.5 m between the rows, which gives an estimated plant density of 5700 plants per hectare.
*Cold hardiness*.—Low chill (USDA plant hardiness Zone 4).
*Cold tolerance*.—Low.
*Chilling requirement*.—Low, estimated between 150 and 300 hours.
*Tolerance to disease*.—None assessed.
*Leafing*.—Overall medium and plant retains leaves during the winter in low chill environments (zone 4).
*Twigginess*.—Low.

FOLIAGE

General:

*Leaf color* (*top side*)—Green group, similar to N137A.
*Leaf color* (*under side*).—Yellow-green, similar to 148D.
*Leaf arrangement*.—Alternate.
*Leaf shape*.—Elliptic.
*Leaf margins*.—Entire.
*Leaf venation*.—Reticulate.
*Leaf length*.—Average 64.7 mm (long to very long).
*Leaf width*.—Average 34.3 mm (broad).
*Leaf length/width ratio*.—1.9.
*Shape of the leaf apex*.—Acute.
*Shape of the leaf base*.—Cuneate.
*Leaf vein color*.—Yellow-green group, similar to 145A.
*Leaf nectaries*.—Absent.
*Pubescence of upper side*.—Absent.
*Pubescence of lower side*.—Absent.
*Attitude*.—Horizontal.

Petioles:

*Length*.—Average 3.4 mm.
*Width*.—Average 1.7 mm.
*Color*.—Similar to yellow-green group 145A.
*Texture*.—Medium to rough.

FLOWERS

General:

*Time of beginning to flower*.—Early season (50% of anthesis estimated to be on the 1st of June, on 3-year-old plants, cultivated at Corindi Beach, NSW).
*Flowering interval on one-year-old shoot*.—June to end of July.

*Flowering interval on current year shoot*.—June to end of July.
*Flower shape*.—Urceolate.
*Flower fragrance*.—Yes, perceptible.

Corolla:
*Shape*.—Urceolate.
*Color*.—White group, similar to NN155B.
*Length*.—Averaging 7.34 mm.
*Width of widest region*.—7 mm.
*Aperture width*.—Narrow, 3.6 mm.
*Anthocyanin coloration of corolla*.—Absent or very weak.
*Corolla ridges*.—Present, average of 5.
*Protrusion of stigma*.—Present.
*Petal width* (*ridge to ridge*).—3.7 mm.
*Corolla/petal texture*.—Smooth.

Calyx (with sepals)
*Diameter*.—4.97 mm.
*Sepal's average number*.—5.
*Shape of the sepal*.—Deltoid.
*Shape apex*.—Acute.
*Margin of the sepal*.—Entire.
*Texture sepal* (*lower side*).—Smooth.
*Texture sepal* (*upper side*).—Smooth.
*Sepal color* (*inside*).—Yellow-green group 144B.
*Sepal color* (*outside*).—Yellow-green group 144C.

Inflorescence:
*Inflorescence length* (*excluding peduncle*).—Short, 15.14 mm.
*Inflorescence width*.—Wide, 20.16 mm.
*Flower length* (*excluding pedicel*).—10.95 mm.
*Flower diameter*.—6.55 mm.
*Flower length/width ratio*.—1.7.
*Surface texture of peduncle*.—Medium (texture between rough and smooth).
*Color of peduncle*.—The base color is similar to yellow-green group 145A, and the overall color is similar to greyed-red group 182A.
*Length of pedicel*.—Short, 6.7 mm.
*Surface texture of pedicel*.—Smooth.
*Color of pedicel*.—Yellow green group, similar to 145B and 145C.
*Number of flowers per cluster*.—Average 8.
*Flower cluster density*.—Dense.
*Flower self-compatibility*.—This variety shows a high percentage of parthenocarpy fruit.

Stamen:
*Length*.—Average 7.7 mm.
*Number per flower*.—9.
*Filament color*.—Similar to yellow-green group 145D.

Pistil:
*Length* (*including ovary*).—Average 12.03 mm.
*Style length* (*including stigma*).—9.15 mm.
*Style color*.—Yellow-green group, similar to 144A.

Anther:
*Length*.—Average 4.4 mm.
*Number per flower*.—9.
*Color*.—Similar to greyed-orange group 165A.

Pollen:
*Abundance*.—Little.
*Color*.—Similar to yellow group 11C.
*Self compatibility*.—Yes (the variety shows a high degree of self-compatibility).

FRUIT

General:
*Time of fruit ripening*.—Early, estimated 50% of the fruit ripe on the 15th of August, on 3-year-old plants, growing at Corindi Beach, NSW.
*Cluster density*.—Dense, average 8 berries per cluster.
*Unripe fruit color*.—Similar to green group 144A.
*Ripe berry color*.—Blue group 103A, when the bloom is removed.
*Berry surface wax abundance*.—Medium.
*Berry weight*.—Very large, on average 4.1 g.
*Berry height from calyx to scar*.—14.3 mm.
*Berry diameter*.—19.6 mm.
*Berry shape*.—Oblate.
*Fruit diameter of calyx basin*.—Small, on average 4.6 mm.
*Fruit depth of calyx basin*.—Shallow.
*Fruit stem scar*.—Small and dry.
*Sweetness when ripe*.—Medium (12 Brix).
*Firmness when ripe*.—Firm to very firm, 200 g/mm, measured with FirmTech.
*Acidity when ripe*.—Medium (0.6%).
*Fruit flesh color*.—Yellow-green 145C.
*Storage quality*.—Very long shelf life (over 38 days).
*Suitability for mechanical harvesting*.—Not tested.
*Self-fruitfulness*.—Yes, with a proportion of the fruit parthenocarpic.
*Uses*.—Fruit to be hand harvested for fresh market.

SEED

General:
*Seed abundance in fruit*.—Low, on average 5 seeds per fruit.
*Seed color*.—Similar to greyed orange 165A.
*Seed length*.—Average 2.14 mm.

COMPARISON WITH SIMILAR CULTIVARS

Table 1 below provides a comparison between 'C12-069' and similar cultivars:

TABLE 1

Comparison of 'C12-069' with similar cultivars

| Characteristic | 'C12-069' | 'C99-42' (U.S. Plant Pat. No. 20,695 P2) | 'Snowchaser' (U.S. Plant Pat. No. 19,503 P3) |
|---|---|---|---|
| Plant vigour | Medium | Weak to medium | Medium |
| Plant growth habit | Upright | Semi-upright to intermediate | Semi-upright |
| One year old shoot length of internodes | Medium | Very short to short | Short |
| Leaf length | Long to very long | short | Long |
| Leaf length (mm) | 64.7 ± 2.6 | 53.10 ± 0.8 | 61.50 ± 0.9 |
| Leaf width | Broad | Very narrow to narrow | Broad |
| Leaf width (mm) | 34.3 ± 1.8 | 22.9 ± 1.3 | 34.3 ± 1.5 |
| Flower size of corolla | Medium | Medium | Medium |
| Flower corolla length (mm) | 9.6 ± 0.3 | 9.7 ± 0.3 | 9.5 ± 0.3 |
| Fruit cluster density | Dense | Sparse | Medium |
| Fruit size | Very large | Small to medium | Small to medium |
| Fruit weight (g) | 4.1 ± 0.2 | 1.9 ± 0.39 | 1.7 ± 0.21 |
| Fruit diameter (mm) | 19.6 ± 1.7 | 15.6 ± 0.96 | 15.10 ± 0.97 |

TABLE 1-continued

| Comparison of 'C12-069' with similar cultivars | | | |
|---|---|---|---|
| Characteristic | 'C12-069' | 'C99-42' (U.S. Plant Pat. No. 20,695 P2) | 'Snowchaser' (U.S. Plant Pat. No. 19,503 P3) |
| Fruit depth of calyx basin | Shallow | Medium | Shallow |
| Fruit intensity of bloom | Medium | Weak to medium | Weak to medium |
| Fruit firmness | Very firm | Firm | Soft |
| Soluble solid content (%) | 12 | 13.1 | 14 |
| Titratable acidity (%) | 0.6 | 0.4 | 0.7 |
| Time of vegetative bud burst | Early | Early | Early |
| Time of beginning of flowering | Early | Early to medium | Very early to early |
| Time of beginning of fruit ripening | Early | Early to medium | Very early to early |

Table 2 below provides a comparison between 'C12-069' and 'FL98-325':

TABLE 2

| Comparison of '02-069' and 'FL98-325' | | |
|---|---|---|
| Characteristic | 'C12-069' | 'FL98-325' (U.S. Plant Pat. No. 26,523) |
| Plant height (m) | 1.44 | 2.0 |
| Calyx diameter (mm) | 4.97 | 5.8 |
| Average fruit diameter of calyx basin (mm) | 4.6 | 6.8 |
| Average fruit cluster density | 8 berries per cluster | 4.1 berries per cluster |
| Fruit surface wax abundance | Medium | Low |
| Fruit weight (g) | 4.1 ± 0.2 | 2.6 |

The invention claimed is:

1. A new and distinct variety of blueberry plant named 'C12-069', substantially as illustrated and described herein.

* * * * *

C12-069

C12-069

C12-069